(12) United States Patent
Goto et al.

(10) Patent No.: US 9,993,629 B2
(45) Date of Patent: Jun. 12, 2018

(54) BALLOON COATING METHOD AND BALLOON COATING APPARATUS

(71) Applicant: TERUMO KABUSHIKI KAISHA, Shibuya-ku, Tokyo (JP)

(72) Inventors: Hiroshi Goto, Kanagawa (JP); Eisuke Furuichi, Kanagawa (JP); Yasuo Kurosaki, Kanagawa-ken (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 0 days. days.

(21) Appl. No.: 15/188,266

(22) Filed: Jun. 21, 2016

(65) Prior Publication Data

US 2016/0296735 A1    Oct. 13, 2016

Related U.S. Application Data

(63) Continuation of application No. PCT/JP2014/083644, filed on Dec. 19, 2014.

(30) Foreign Application Priority Data

Dec. 21, 2013    (JP) ................................ 2013-264708

(51) Int. Cl.
*A61M 25/10*    (2013.01)
*B05B 12/00*    (2018.01)

(52) U.S. Cl.
CPC ......... *A61M 25/1029* (2013.01); *B05B 12/00* (2013.01); *A61M 25/10* (2013.01);
(Continued)

(58) Field of Classification Search
CPC ........................................... A61M 2025/1031
(Continued)

(56) References Cited

U.S. PATENT DOCUMENTS 6,613,066 B1    9/2003  Fukaya et al.
2009/0093870 A1*  4/2009  Menendez ............... B05D 1/02
                                                    623/1.11
(Continued)

FOREIGN PATENT DOCUMENTS

WO          2009135125 A2    11/2009
WO    WO 2013/181498 A1    12/2013

OTHER PUBLICATIONS

International Search Report (PCT/ISA/210) dated Feb. 10, 2015, by the Japanese Patent Office as the International Searching Authority for International Application No. PCT/JP2014/083644.

(Continued)

*Primary Examiner* — Cachet I Sellman
(74) *Attorney, Agent, or Firm* — Buchanan Ingersoll & Rooney PC

(57) ABSTRACT

A balloon coating method and apparatus are disclosed which can perform coating while freely controlling, for example, the thickness of a coating layer and/or the morphological form of a drug. The balloon coating method and the balloon coating apparatus are for forming a coating layer on a surface of a balloon. The balloon coating method includes a pulling step of pulling the balloon in the direction of an axis of the balloon to thereby straighten a bend of the balloon, and a coating step of rotating the balloon about the axis of the balloon, with the balloon maintained in the bend-straightened state, and coating an outer surface of the balloon with a coating liquid containing a drug.

20 Claims, 5 Drawing Sheets

(52) U.S. Cl.
CPC ............... *A61M 2025/105* (2013.01); *A61M 2025/1031* (2013.01)

(58) Field of Classification Search
USPC .......................... 118/33; 427/171, 2.24, 2.25
See application file for complete search history.

(56) References Cited

U.S. PATENT DOCUMENTS

| | | | |
|---|---|---|---|
| 2010/0040766 A1* | 2/2010 | Chappa | ............... B05B 13/0214 427/2.3 |
| 2010/0055294 A1 | 3/2010 | Wang et al. | |
| 2011/0281020 A1 | 11/2011 | Gong et al. | |
| 2012/0128863 A1* | 5/2012 | Nguyen | ............ A61M 25/1029 427/2.3 |
| 2013/0337147 A1 | 12/2013 | Chappa et al. | |

OTHER PUBLICATIONS

Extended European Search Report dated Jun. 30, 2017 in corresponding European Patent Application No. 14872289.5.

\* cited by examiner

BALLOON COATING METHOD AND BALLOON COATING APPARATUS

CROSS-REFERENCES TO RELATED APPLICATIONS

This application is a continuation of International Application No. PCT/JP2014/083644 filed on Dec. 19, 2014, and claims priority to Japanese Application No. 2013-264708 filed on Dec. 21, 2013, the entire content of both of which is incorporated herein by reference.

TECHNICAL FIELD

The present disclosure relates to a balloon coating method and a balloon coating apparatus for forming a coating layer on a surface of a balloon.

BACKGROUND ART

In recent years, balloon catheters have been used for improving lesion affected areas (stenosed parts) generated in body lumens. A balloon catheter can include an elongate shaft portion, and a balloon, which is provided on the distal side of the shaft portion and is inflatable in the radial direction. After the balloon in a deflated state is brought to a target site in the body by way of a thin body lumen, the balloon is inflated, whereby the lesion affected area can be pushed wide open.

If a lesion affected area is forcibly pushed open, however, excessive proliferation of endothelial cells may occur, causing new stenosis (restenosis). In view of this, recently, drug eluting balloons wherein an outer surface of a balloon is coated with a drug for restraining stenosis have been used. The drug eluting balloon, by being inflated, is able to instantaneously release the drug contained in the coating on the outer surface thereof to the lesion affected area and transfer the drug to the living body tissue, thereby restraining restenosis.

A variety of methods have been proposed for coating a balloon with a drug. For instance, U.S. Patent Application Publication No. 2010/055294 describes a method in which a coating liquid containing a drug is supplied to a surface of a balloon while the coating quantity is being controlled and the balloon is being rotated and being moved in an axial direction, and the coating liquid is dried to form a coating layer containing the drug.

If the balloon is bent along the axial direction when the balloon surface is coated with the drug while being rotated, the balloon gets eccentric when the balloon is rotated. The bending of the balloon arises from differences between the balloon and a shaft portion in material and/or thickness, variations in expansion/contraction ratio from part to part upon inflation of the balloon, and the like. The influence of bending is great especially in a balloon that is long in the axial direction. When the balloon is bent to get eccentric, the distance from the distal end of a dispensing tube for supplying the coating liquid to the outer surface of the rotating balloon varies with rotation, making it difficult to uniformly coat the outer surface of the balloon with the drug. Further, the drug in the coating on the outer surface of the balloon can assume different morphological forms such as crystalline form, amorphous form and mixed forms thereof depending on the length of time of volatilization of the solvent, etc. When it becomes difficult to achieve uniform coating with the drug, the volatilization of the solvent may become non-uniform, possibly making it difficult to control the formation of the morphological form. Neither of the crystalline form and the amorphous form is more desirable than the other, and it can be desirable that the morphological form of the drug can be selected according to the purpose

SUMMARY

A balloon coating method and a balloon coating apparatus are disclosed by which coating can be performed while freely controlling the thickness of a coating layer, or the morphological form of a drug.

A balloon coating method is disclosed for forming a coating layer on an outer surface of a balloon of a balloon catheter, the balloon coating method including: a pulling step of pulling the balloon in an axial direction of the balloon to thereby straighten a bend of the balloon; and a coating step of rotating the balloon about an axis of the balloon, with the balloon maintained in a bend-straightened state, and coating the outer surface of the balloon with a coating liquid containing a drug.

In the balloon coating method configured as above, the outer surface of the balloon is coated with the coating liquid while the balloon is being rotated in a state where the bend of the balloon is straightened. Therefore, variability of the thickness of the coating liquid can be suppressed, making it easy to control the thickness of the coating liquid (the coating layer). In addition, by regulating the thickness of the coating liquid, it becomes relatively easy to control the time of volatilization of the solvent, so that, for example, the morphological form of the drug in the coating layer can be freely controlled.

Where a pulling force can be controlled arbitrarily in the pulling step, the pulling force can be set to a desirable pulling force according to the balloon and to appropriately straighten the bend of the balloon.

Where a member for applying a pulling force to the balloon is rotated at the same rotational speed as that of the balloon, by a second rotating mechanism different from a rotating mechanism for rotating the balloon, in the coating step, the rotation of the balloon is stabilized and the balloon can be retrained from being deformed due to a twisting force or the like. Consequently, variability of the thickness of the coating liquid can be suppressed, making it relatively easy to control the thickness of the coating liquid.

Where the balloon is straightened such that a deflection amount of the balloon is not more than 0.5 mm in the pulling step, an outer circumferential surface of the rotating balloon can be uniformly coated with the coating liquid.

Where a pulling force is applied to the balloon through an elastic member in the pulling step, a suitable pulling force can be easily set while lightening the load on the balloon by restraining an excessive load from acting on the balloon.

Where a balloon coating apparatus for forming a coating layer on an outer surface of a balloon of a balloon catheter can include: a rotating mechanism for rotating the balloon about an axis of the balloon; a pulling mechanism for pulling the balloon in an axial direction of the balloon, with the balloon maintained in a rotatable state; and a coating mechanism for coating the outer surface of the balloon with a coating liquid containing a drug, the outer surface of the balloon can be coated with the coating liquid by the coating mechanism while rotating the balloon by the rotating mechanism in the state where the bend of the balloon is straightened by applying a pulling force to the balloon by the pulling mechanism. In this case, variability of the thickness of the coating liquid can be suppressed, and it can be relatively easy to control the thickness of the coating liquid. In addition, since the thickness of the coating liquid can be regulated, the time of volatilization of the solvent can be easily controlled, so that, for example, the morphological form and/or size of the drug in the coating layer can be freely controlled.

Where the pulling mechanism is capable of arbitrarily controlling the pulling force, the pulling force can be set to a desirable pulling force according to the balloon and to appropriately straighten the bend of the balloon.

Where the balloon coating apparatus further can include a second rotating mechanism that rotates a member for applying a pulling force to the balloon at the same rotational speed as that of the balloon, the rotation of the balloon is stabilized, and the balloon can be restrained from being deformed due to a twisting force or the like. Accordingly, variability of the thickness of the coating liquid can be suppressed, and it can be relatively easy to control the thickness of the coating liquid.

Where the pulling mechanism can include an elastic member for applying a pulling force to the balloon, an appropriate pulling force can be easily set by the elastic member while lightening the load on the balloon by restraining an excessive load from acting on the balloon.

A balloon coating method is disclosed for forming a coating layer on an outer surface of a balloon of a balloon catheter, the balloon coating method comprising: pulling the balloon in an axial direction of the balloon to thereby straighten a bend of the balloon; rotating the balloon about an axis of the balloon; maintaining the balloon in a bend-straightened state; and coating the outer surface of the balloon with a coating liquid containing a drug.

DESCRIPTION OF EMBODIMENTS

Figure 1:
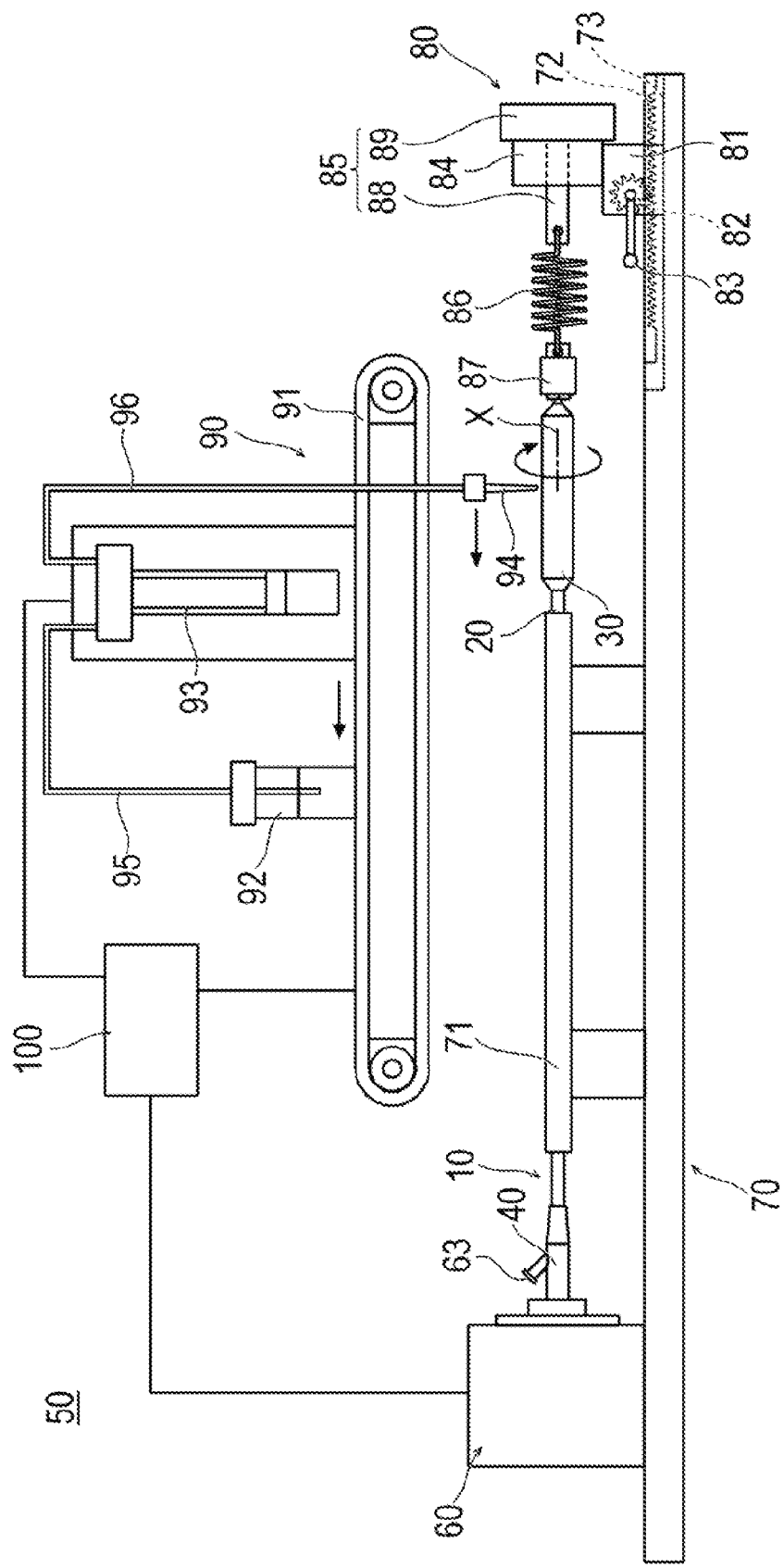
FIG. 1 is a schematic view showing an apparatus for carrying out a balloon coating method according to a first embodiment of the present disclosure.

Embodiments of the present disclosure will be described below, referring to the drawings. Note that the dimensional ratios in the drawings may be exaggerated for convenience of explanation and may therefore be different from the actual ratios.

A balloon coating method according to a first embodiment of the present disclosure is for forming a coating layer containing a drug on a surface of a balloon, and is carried out by a balloon coating apparatus 50 illustrated in FIG. 1. Note that herein the side on which a balloon catheter 10 is inserted into a body lumen will be referred to as "distal end" or "distal side," and the side of an operator's hand operation will be referred to as "proximal end" or "proximal side."

Figure 2:
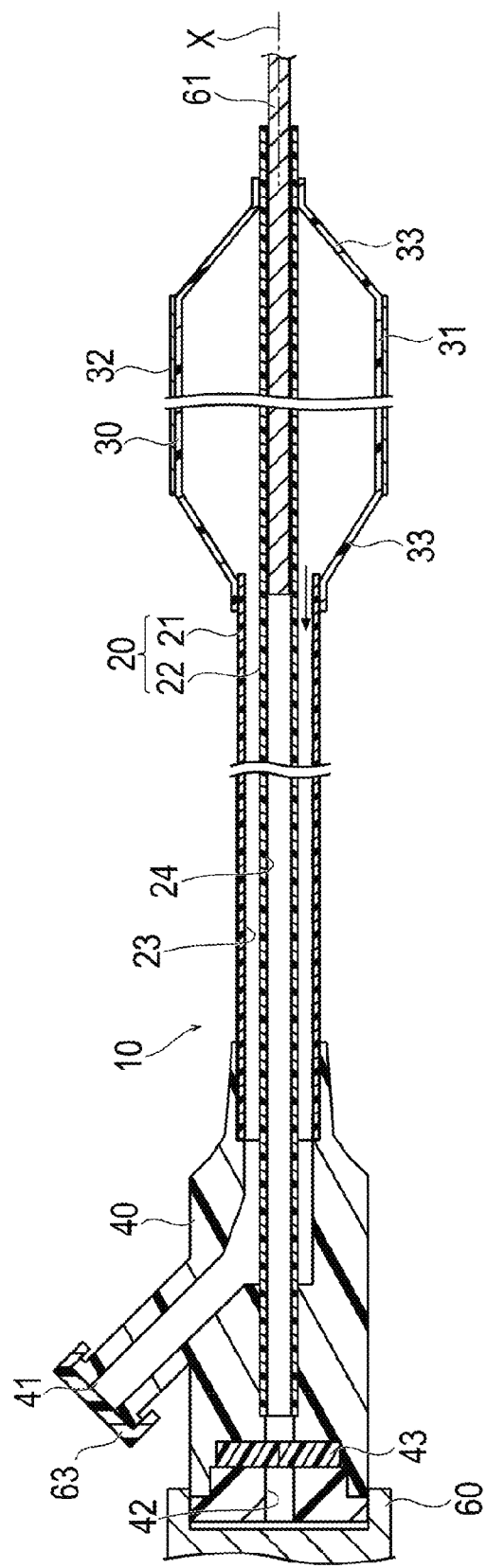
FIG. 2 is a sectional view showing a balloon catheter.

In the first place, the structure of the balloon catheter 10 will be described. As shown in FIG. 2, the balloon catheter 10 can include an elongate catheter main body section 20, a balloon 30 provided at a distal portion of the catheter main body section 20, and a hub 40 firmly attached to a proximal end of the catheter main body section 20.

The catheter main body section 20 can include an outer tube 21 which is a tube-shaped body opening at a distal end and a proximal end thereof, and an inner tube 22 disposed inside the outer tube 21. Between the outer tube 21 and the inner tube 22 is formed an inflation lumen 23 through which an inflation fluid flows for inflating the balloon 30. Inside the inner tube 22 is formed a guide wire lumen 24 in and through which a guide wire is inserted and passes through.

The balloon 30 is adhered to the inner tube 22 on a distal side, and is adhered to the outer tube 21 on a proximal side, and the inside of the balloon 30 communicates with the inflation lumen 23. The balloon 30 is formed, at a central portion in the direction of an axis X thereof, with a cylindrical straight portion 31 having a constant outside diameter when inflated, and is formed, on both sides in the direction of the axis X of the straight portion 31, with tapered portions 33 which are gradually varied in outside diameter. A coating layer 32 containing a drug can be formed on the whole part of an outer surface of the straight portion 31. Note that the range of formation of the coating layer 32 on the balloon 30 is not limited to only the straight portion 31 but may include at least part of the tapered portions 33 in addition to the straight portion 31, or may be only part of the straight portion 31.

The hub 40 can include a first opening portion 41 that functions as a port which communicates with the inflation lumen 23 of the outer tube 21 and through which the inflation fluid can flow in and out, and a second opening portion 42 in and through which the guide wire lumen 24 is inserted and passes through. A blood stop valve 43 for inhibiting blood from flowing out is provided at the second opening portion 42.

The balloon 30 is preferably formed from a material, which has a certain degree of flexibility. Examples of such a usable material include thermoplastic resins such as polyolefins such as polyethylene, polypropylene, polybutene, ethylene-propylene copolymers, ethylene-vinyl acetate copolymers, ionomers, and mixtures of two or more of them, flexible polyvinyl chloride resin, polyamides, polyamide elastomers, polyesters, polyester elastomers, polyurethanes, fluororesins, silicone rubbers, and latex rubber.

The balloon 30 may be bent along the direction of the axis X thereof; particularly, where the length of the balloon 30 is not less than, for example, 100 mm, the balloon 30 is liable to bend. One of the causes of bending of the balloon 30 is considered to be a difference in expansion/contraction ratio upon inflation of the balloon 30, the difference arising from differences between the catheter main body section 20 and the balloon 30 in material or thickness, in the manufacturing process of the balloon catheter 10.

The balloon coating apparatus 50 will be described next. As depicted in FIG. 1, the balloon coating apparatus 50 can include a rotating mechanism 60 for holding and rotating the balloon catheter 10 about the axis X of the balloon 30, a support base 70 for supporting the balloon catheter 10 in a rotatable manner, a pulling mechanism 80 for pulling the balloon 30 in a direction along the axis X of the balloon 30, a coating mechanism 90 for coating a surface of the balloon 30 with a coating liquid R, and a control mechanism 100 for controlling the balloon coating apparatus 50.

The rotating mechanism 60 holds the hub 40 of the balloon catheter 10, and rotates the balloon catheter 10 by a drive source, such as a motor, incorporated in the balloon coating apparatus 50. The balloon catheter 10 has a core member 61 (see FIG. 2) inserted and held in the guide wire lumen 24, and flowing-in of the coating liquid R into the guide wire lumen 24 is prevented by the core member 61. In addition, the balloon catheter 10 has a cap 63 put on the first opening portion 41 of the hub 40 in such a manner as to cover the inflation lumen 23, whereby the inflation fluid can be sealed when the balloon 30 is inflated.

The support base 70 can include a tube-shaped support section 71 in which the catheter main body section 20 is accommodated and supported in a rotatable manner. In addition, the support base 70 can include a groove portion 72 for holding the pulling mechanism 80 such that the pulling mechanism 80 can be moved rectilinearly, and a rack 73 having teeth arrayed rectilinearly.

The pulling mechanism 80 can include a sliding portion 81 fitted to the groove portion 72 of the support base 70, a pinion 82 meshed with the rack 73, a handle 83 for rotating the pinion 82, a bearing portion 84 fixed to the sliding portion 81, a pulling member 85 held on the bearing portion 84, an elastic member 86 interlocked to the pulling member 85, and an interlock portion 87 interlocking the elastic member 86 and the balloon 30 to each other.

The sliding portion 81 is slidably fitted in the groove portion 72 of the support base 70, and, by sliding within the groove portion 72, moves the bearing portion 84 rectilinearly. The pinion 82 can be rotated by a rotating operation of the handle 83, and, by meshing with the rack 73, can move the sliding portion 81 along the groove portion 72. Note that the handle 83 can be controlled by providing a motor, instead of rotating the handle 83 by a manual rotating operation.

The bearing portion 84 is configured by combining a thrust bearing capable of bearing a thrust load with a radial bearing capable of bearing a radial load. Note that a bearing capable of bearing both a thrust load and a radial load, such as an angular contact ball bearing, may also be used. Since the bearing portion 84 can bear both a thrust load and a radial load, the bearing portion 84 can apply an axial force to the pulling member 85 while the pulling member 85 is being held in a rotatable manner.

The pulling member 85 can include a rotary shaft 88 penetrating the bearing portion 84, and a large diameter portion 89 which is formed at an end portion of the rotary shaft 88 to be greater than the rotary shaft 88 in diameter and which contacts the bearing portion 84 from a thrust direction. The large diameter portion 89 contacts the bearing portion 84 from the thrust direction, and can apply an axial pulling force to the rotary shaft 88 even while rotating.

The elastic member 86 can be a coil spring, of which one end is interlocked to an end portion of the rotary shaft 88 such as to be rotatable together with the rotary shaft 88, and the other end is interlocked to an end portion of the interlock portion 87 such as to be rotatable together with the interlock portion 87. Note that the elastic member 86 is not particularly limited in material or configuration, so long as the elastic member 86 can, by elastically deforming, apply a pulling force; thus, the elastic member 86 may be, for example, a rubber. The pulling force applied to the balloon 30 is preferably set appropriately in such a manner as not to damage the balloon 30 and as to be able to restrain the balloon 30 from getting eccentric. For example, the pulling force can be several newtons, but is not particularly limited.

The interlock portion 87 is a chuck device such as a mechanical chuck, a magnetic chuck or a vacuum chuck, and can clamp a distal-side end portion of the balloon 30 in the manner of clamping the balloon 30 from radially outer sides. Note that the interlock portion 87 is not particularly restricted in configuration, so long as the interlock portion 87 can hold the balloon 30. In addition, so long as the interlock portion 87 can pull the balloon 30, the interlock portion 87 may not necessarily clamp the balloon 30 itself but may clamp, for example, the inner tube 22 located on the distal side of the balloon 30. Examples of the material which can be used to constitute the interlock portion 87, can include metals such as stainless steel, aluminum, resins such as fluororesins, acrylonitrile-butadiene-styrene resin, polyethylene, and rubbers.

The coating mechanism 90 can include a movable base 91 movable rectilinearly in a direction parallel to the axis X of the balloon 30, a vessel 92 accommodating the coating liquid R, a liquid feed pump 93 for feeding the coating liquid R in an arbitrary feed quantity, and a coating section 94 for coating the balloon 30 with the coating liquid R.

The movable base 91 can be rectilinearly moved in both directions along the axis X of the balloon catheter 10, by a drive source such as a motor incorporated in the balloon coating apparatus 50.

The liquid feed pump 93 is, for example, a syringe pump, which is controlled by the control mechanism 100. The liquid feed pump 93 can suck the coating liquid R from the vessel 92 through a suction tube 95, and can supply the coating liquid R to the coating section 94 through a supply tube 96 in an arbitrary liquid feed quantity. The liquid feed pump 93 is disposed on the movable base 91, and can be moved rectilinearly by movement of the movable base 91. Note that the liquid feed pump 93 is not limited to the syringe pump so long as it can feed the coating liquid R; for example, it may be a tube pump.

The coating section 94 is a dispensing tube which ejects the coating liquid R from an opening portion opening toward an outer surface of the balloon 30. The opening portion of the coating section 94 is formed to open in a plane orthogonal to an axis of the coating section 94, but this is not restrictive. The coating section 94 can be rectilinearly moved in both directions along the axis X of the balloon catheter 10, together with the liquid feed pump 93 disposed on the movable base 91. Note that the coating section 94 may not be the dispensing tube, so long as it can coat the outer surface of the balloon 30 with the coating liquid R; for example, the coating section 94 may be a porous body such as fibrous material, woven fabric, nonwoven fabric, sponge, impregnated with the coating liquid R, a spatula-like member, or a brush.

The control mechanism 100 is composed, for example, of a computer, and generally controls the rotating mechanism 60 and the coating mechanism 90.

The coating liquid R contains a drug, an additive or additives, and a volatile solvent. The drug is a substance which can act on a living body, and may be either a water-soluble drug or a water-insoluble drug. From the viewpoint of restraining elution of the drug into blood, the drug is preferably a water-insoluble drug.

The water-insoluble drug means a drug which is insoluble or difficulty soluble in water; specifically, for example, the solubility of the drug in water is less than 5 mg/mL at pH 5 to 8. The solubility may, for example, be less than 1 mg/mL, or, further, may be less than 0.1 mg/mL. The water-insoluble drug can include fat-soluble drug.

Some examples of the preferred water-insoluble drug include immunosuppressant, for example, cyclosporines inclusive of cyclosporine, immunoadjuvant such as rapamycin, carcinostatic agent such as paclitaxel, antiviral or antibacterial agent, antineoplastic agent, analgesic agent, antiinflammatory agent, antibiotic, antiepileptic, anxiolytic agent, antianesthetic agent, antagonist, neuron blocking agent, anticholinergic agent, antiarrhythmic agent, antihypertensive agent, hormone preparation, and nutritional supplement.

The water-insoluble drug is preferably at least one selected from rapamycin, paclitaxel, docetaxel, and everolimus. The rapamycin, paclitaxel, docetaxel and everolimus herein include their analogs and/or derivatives so long as the analogs and/or derivatives have equivalent drug activity to the original. For example, paclitaxel and docetaxel are in an analog relation. Rapamycin and everolimus are in a derivative relation. Among these, more preferable is paclitaxel.

The coating liquid R in this embodiment preferably contains the water-insoluble drug in a concentration, for example, of 5 mg/mL to 60 mg/mL, more preferably in a concentration of 20 mg/mL to 50 mg/mL, and further preferably in a concentration of 30 mg/mL to 40 mg/mL.

The additive is not particularly limited, and polymers and/or high molecular or low molecular compounds that form solid dispersion bodies with the drug are applicable. For example, the additive is preferably at least one selected from the group consisting of polyolefins, polyisobutylene, ethylene-α-olefin copolymer, acrylic polymers and copolymers, polyvinyl chloride, polyvinyl methyl ether, polyvinylidene fluoride, polyvinylidene chloride, polyacrylonitrile, polyvinyl ketone, polystyrene, polyvinyl acetate, ethylene-methyl methacrylate copolymer, acrylonitrile-styrene copolymer, ABS resin, nylon 12 and block copolymers thereof, polycaprolactone, polyoxymethylene, polyesters, polyethers, polyamides, epoxy resin, polyurethane, rayon triacetate, cellulose, cellulose acetate, cellulose butyrate, cellophane, cellulose nitrate, propionyl cellulose, cellulose ether, carboxymethyl cellulose, chitin, polylactic acid, polyglycolic acid, polyethylene oxide, polylactic acid-polyethylene oxide copolymer, polyethylene glycol, polypropylene glycol, glycerol, polyvinyl alcohol, polyvinyl pyrrolidone, organic acids, and organic acid esters. Note that the additive may not be provided.

The additive is preferably used in a small amount relative to the drug, and preferably does not form a matrix. In addition, the additive preferably does not include, but may include, micelles, liposome, contrast agent, emulsifier, or surfactant. In addition, the additive preferably can include only a low molecular compound or compounds, without including a polymer.

The volatile solvent is not specifically restricted, and preferably can include at least one of volatile organic solvents such as methanol, ethanol, dioxane, tetrahydrofuran, dimethyl formamide, acetonitrile, dimethyl sulfoxide, acetone. In addition, the volatile organic solvent may be mixed with water or the like.

A balloon coating method for forming a coating layer 32 containing the drug on a surface of the balloon 30 by use of the aforementioned balloon coating apparatus 50 will be described below.

First, an inflation fluid is supplied via the first opening portion 41 of the balloon catheter 10 into the balloon 30 to inflate the balloon 30, and, in this condition, the first opening portion 41 is sealed by putting the cap 63 thereon, to thereby maintain the inflated state of the balloon 30. Note that the coating layer 32 can also be formed on the surface of the balloon 30 without inflating the balloon 30, in which case it is unnecessary to supply the inflation fluid into the balloon 30.

Next, the balloon catheter 10 is disposed on the support base 70 in a rotatable manner, and the hub 40 is interlocked to the rotating mechanism 60. Then, a distal-side end portion of the balloon 30 is clamped by the interlock portion 87.

Thereafter, by a rotating operation of the handle 83, the pinion 82 meshed with the rack 73 is rotated, whereby the sliding portion 81 is moved along the groove portion 72 in a direction for spacing away from the balloon 30. This causes the large diameter portion 89 to move by being pushed by the bearing portion 84 in a direction for spacing away from the balloon 30. As a result, the rotary shaft 88 configured to be integral with the large diameter portion 89 is moved in a direction for spacing away from the balloon 30, and the elastic member 86 located between the rotary shaft 88 and the interlock portion 87 is extended, whereby a pulling force can be applied to the balloon 30 interlocked with the interlock portion 87 (pulling step). Since the pulling force acting on the balloon 30 increases as the elastic member 86 is extended, the pulling force can be set arbitrarily by regulating the moving amount of the sliding portion 81. By this operation, the balloon 30 is put into a rectilinearly extending state as its bend is straightened. In order that the coating liquid R can be uniformly applied to an outer circumferential surface of the balloon 30 in rotation, the deflection amount of the balloon 30 after straightening of the bend is preferably, for example, not more than 0.5 mm, more preferably not more than 0.3 mm. The deflection amount can be easily measured, for example, by a method wherein the balloon 30 is rotated one revolution with a probe of a dial gauge put in contact with the balloon 30 from a radially outer side, and the difference between a maximum value and a minimum value of retraction amount (moving amount) of the probe is determined. Alternatively, the deflection amount may be measured, for example, by use of a non-contact type laser displacement sensor, in order that the balloon 30 is not deformed.

Subsequently, the movable base 91 is moved to locate the coating section 94 at a position on the distalmost side of a range where the coating layer 32 is to be formed on the balloon 30, and the balloon catheter 10 is rotated by the rotating mechanism 60. When the balloon 30 is rotated, the interlock portion 87 grasping the balloon 30, the elastic member 86 and the pulling member 85 are also rotated together with the balloon 30, since the pulling member 85 is rotatably held by the bearing portion 84. In this case, since the bearing portion 84 can bear a thrust load, the state where a pulling force is applied to the balloon 30 can be maintained, whereby the balloon 30 can be rotated in the state where the bend of the balloon 30 is straightened.

Next, the coating liquid R is supplied to the coating section 94 while the coating quantity is regulated by the liquid feed pump 93 of the coating mechanism 90, and the movable base 91 is moved to gradually move the coating section 94 in the proximal direction (coating step). The moving velocity of the coating section 94 can be, for example, 0.5 mm/second to 10 mm/second, which is not restrictive. The ejection rate of the coating liquid R from the coating section 94 can be, for example, 0.05 μL/second to 5 μL/second, which is not restrictive. The rotational speed of the balloon 30 can be, for example, 20 rpm to 100 rpm, which is not limitative.

Thereafter, the volatile solvent contained in the coating liquid R applied to the surface of the balloon 30 volatilizes, whereby the coating layer 32 containing the drug and the additive or additives is gradually formed on the surface of the balloon 30. The time of volatilization is appropriately set according to the solvent, and can be, for example, on the order of several seconds to several tens of seconds.

In the coating step, the outer surface of the balloon 30 is coated with the coating liquid R while the balloon 30 is being rotated in the condition where bend of the balloon 30 is straightened by applying the pulling force to the balloon 30. Therefore, variability of the thickness of the coating liquid R can be suppressed, and the thickness of the coating liquid R (the coating layer 32) can be easily controlled.

In addition, by regulating the thickness of the coating liquid R, the time of volatilization of the solvent can be easily controlled, and, for example, the morphological form and/or size of the drug in the coating layer 32 can be freely controlled. The drug in the coating formed on the outer surface of the balloon 30 can assume different morphological forms such as crystalline form, amorphous form and mixed forms thereof. Even in the case where the drug is of the crystalline form, there may exist various morphological forms that differ in crystal structure. Further, the crystals and amorphous phases may be laid out regularly or may be laid out irregularly, in the coating layer 32. Such a morphological form of the drug is influenced by the length of time of volatilization of the volatile solvent and the ambient temperature. For this reason, by appropriately setting the volatilization time, the morphological form of the drug contained in the coating layer 32 can be freely controlled.

In addition, the coating section 94 can be gradually moved in the direction of the axis X while the balloon 30 is being rotated, whereby the coating layer 32 is gradually formed on the outer surface of the balloon 30. After the coating layer 32 is formed on the whole part of the range of coating of the balloon 30, the rotating mechanism 60 and the coating mechanism 90 are stopped.

The thickness of the coating layer 32 can be, for example, 1 μm to 50 μm, which is not limitative. The thickness can be appropriately set according to the size, use and the like of the balloon 30.

Thereafter, the balloon catheter 10 is dismounted from the balloon coating apparatus 50, and the coating of the balloon 30 is completed.

As aforementioned, the balloon coating method according to this embodiment is a balloon coating method for forming a coating layer 32 on an outer surface of a balloon 30 of a balloon catheter 10, wherein the method can include a pulling step of pulling the balloon 30 in the direction of the axis X of the balloon 30 to thereby straighten a bend of the balloon 30; and a coating step of rotating the balloon 30 about the axis X of the balloon 30, while maintaining the balloon 30 in the bend-straightened state, to thereby coat the outer surface of the balloon 30 with a coating liquid R containing a drug. Therefore, the outer surface of the balloon 30 can be coated with the coating liquid R while rotating the balloon 30 in the condition where the bend of the balloon 30 is straightened by applying the pulling force to the balloon 30. For this reason, variability of the thickness of the coating liquid R can be suppressed, and the thickness of the coating liquid R (the coating layer 32) can be easily controlled. In addition, by regulating the thickness of the coating liquid R, the time of volatilization of the solvent can be easily controlled, and the morphological form and/or size of the drug in the coating layer 32 can be freely controlled.

In addition, in the pulling step, the pulling force is applied to the balloon 30 through the elastic member 86. As compared to the case where the balloon 30 is pulled directly by the pulling member 85 without the presence of the elastic member 86, therefore, an appropriate pulling force can be easily set, while lightening the load on the balloon 30 by restraining an excessive load from acting on the balloon 30.

In addition, since the pulling force can be arbitrarily regulated in the pulling step, the pulling force can be set to a desirable pulling force according to the balloon 30, and thereby to appropriately straighten the bend of the balloon 30.

In addition, since the bend of the balloon 30 is straightened in the pulling step in such a manner that the deflection amount of the balloon 30, for example, will not be more than 0.5 mm, and the coating liquid R can be uniformly applied to the outer circumferential surface of the rotating balloon 30.

In addition, the balloon coating apparatus 50 in this embodiment is an apparatus for forming a coating layer 32 on an outer surface of a balloon 30 of a balloon catheter 10, wherein the apparatus can include a rotating mechanism 60 for rotating the balloon 30 about the axis X of the balloon 30, a pulling mechanism 80 for pulling the balloon 30 in the direction of the axis X of the balloon 30, with the balloon 30 kept in a rotatable state, and a coating mechanism 90 for coating the outer surface of the balloon 30 with a coating liquid R containing a drug. Therefore, the outer surface of the balloon 30 can be coated with the coating liquid R by the coating mechanism 90 while the balloon 30 is being rotated by the rotating mechanism 60 in the condition where the bend of the balloon 30 is straightened by applying a pulling force to the balloon 30 by the pulling mechanism 80. Accordingly, it is possible to suppress variability of the thickness of the coating liquid R, and thereby to easily control the thickness of the coating liquid R (the coating layer 32). In addition, by regulating the thickness of the coating liquid R, the time of volatilization of the solvent can be easily controlled, and it is possible to freely control, for example, the morphological form and/or size of the drug in the coating layer 32.

In addition, the pulling mechanism 80 has the elastic member 86 for applying the pulling force to the balloon 30. As compared with the case where the balloon 30 is pulled directly by the pulling member 85 without the presence of the elastic member 86, therefore, an appropriate pulling force can be easily set by the elastic force 86 while lightening the load on the balloon 30 by restraining an excessive load from acting on the balloon 30.

In addition, since the pulling mechanism 80 can arbitrarily control the pulling force, the pulling force can be set to a desirable pulling force according to the balloon 30.

Figure 3:
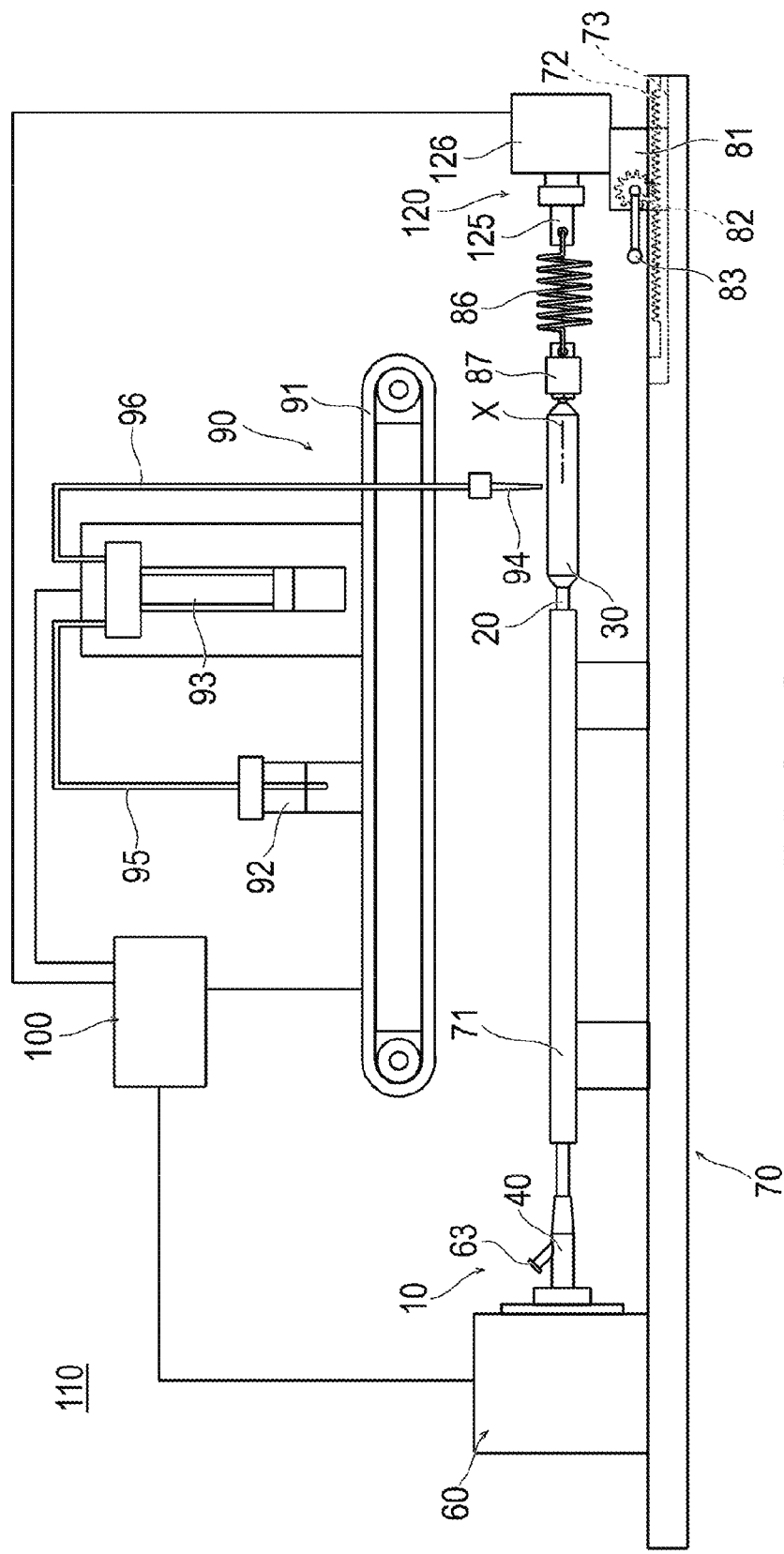
FIG. 3 is a schematic view showing an apparatus for carrying out a balloon coating method according to a second embodiment of the present disclosure.

A balloon coating method according to a second embodiment of the present disclosure is carried out by a balloon coating apparatus 110 illustrated in FIG. 3. Note that the parts having the same or equivalent functions to those in the first embodiment are denoted by the same reference symbols as used above, and descriptions of these parts will be omitted.

A pulling mechanism 120 of the balloon coating apparatus 110 can include a pulling member 125 interlocked to an elastic member 86, and a second rotating mechanism 126 for rotating the pulling member 125. The second rotating mechanism 126, controlled by a control mechanism 100, rotates the pulling member 125 at the same rotational speed (the same revolving speed) as that of the balloon 30 in synchronism with the rotating mechanism 60. Therefore, while the elastic member 86, the pulling member 85 and the interlock portion 87 which apply a pulling force to the balloon 30 in the coating step are rotated by a rotating force received from the balloon 30 in the balloon coating apparatus 50 in the first embodiment, the elastic member 86, the pulling member 125 and the interlock portion 87 in the balloon coating apparatus 110 in the second embodiment are rotated at the same rotational speed as that of the balloon 30 by a rotating force applied by the second rotating mechanism 126. For this reason, the rotation of the balloon 30 can be stabilized, the balloon 30 can be restrained from being deformed by an unnecessary force such as a twisting force acting thereon. Consequently, variability of the thickness of the coating liquid R can be suppressed, and the thickness of the coating liquid R (the coating layer 32) can be easily controlled.

Note that the configuration of the second rotating mechanism is not specifically restricted, so long as the second rotating mechanism can impart a rotating force to a member that applies a pulling force to the balloon 30. For example, a common drive source (motor or the like) may be used for both the first rotating mechanism and the second rotating mechanism.

Figure 4:
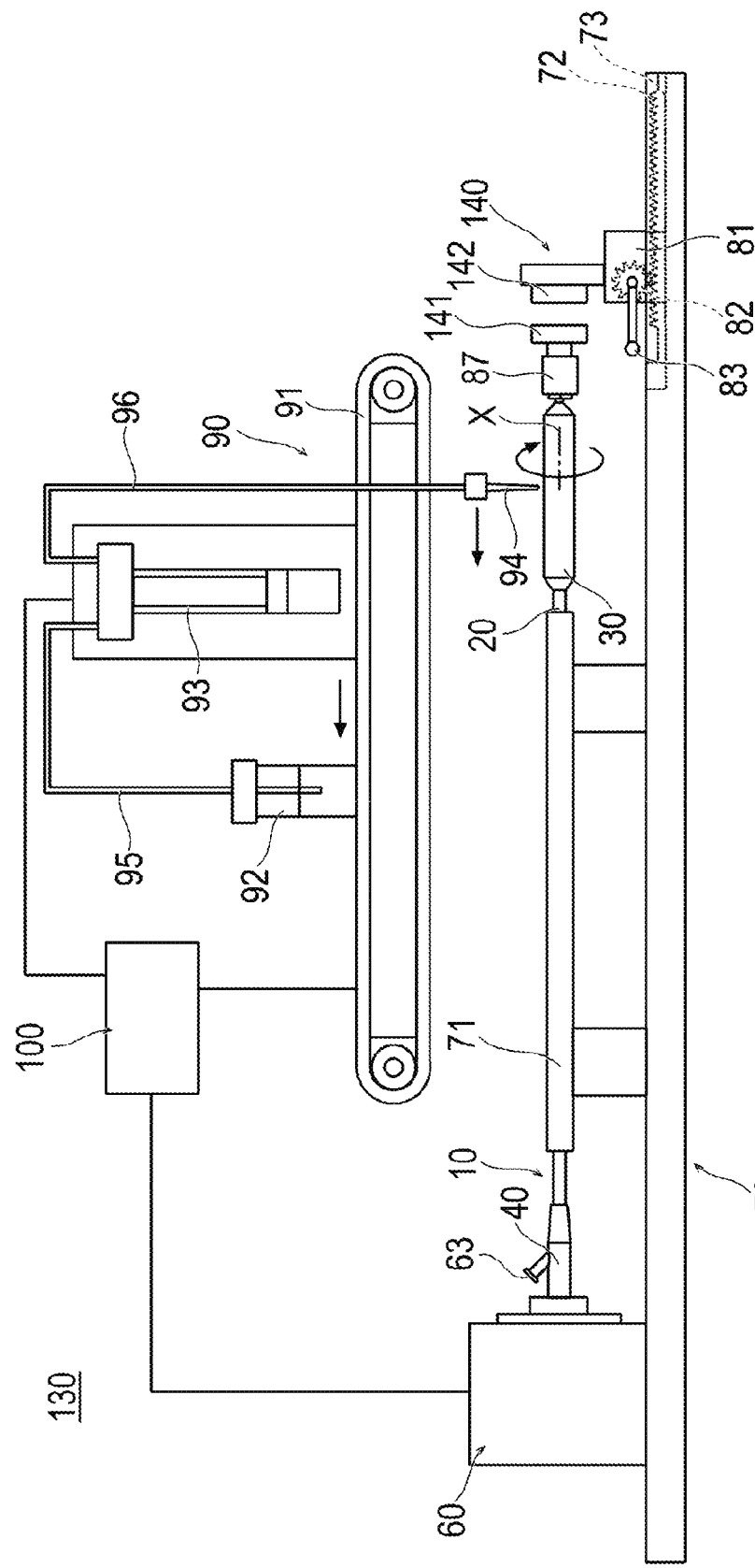
FIG. 4 is a schematic view showing an apparatus for carrying out a balloon coating method according to a third embodiment of the present disclosure.

A balloon coating method according to a third embodiment of the present disclosure is carried out by a balloon coating apparatus 130 shown in FIG. 4. Note that the parts having the same or equivalent functions to those in the first embodiment are denoted by the same reference symbols as used above, and descriptions of these parts will be omitted.

A pulling mechanism 140 of the balloon coating apparatus 130 has a first magnet 141 provided on the side opposite to the side of interlock with the balloon 30 of an interlock portion 87, and a second magnet 142 provided at such a position as to face the first magnet 141. The second magnet 142 is disposed on a sliding portion 81. The first magnet 141 and the second magnet 142 are arranged in such a manner that their different poles face each other, whereby they are attracted by each other. Therefore, in the balloon coating apparatus 130 in the third embodiment, even when the first magnet 141 interlocked to and rotated together with the balloon 30 is rotated, a pulling force can be applied to the balloon 30 without the second magnet 142 being rotated. Accordingly, it is unnecessary to provide a bearing, and this assembly can be easily configured. In addition, the distance between the first magnet 141 and the second magnet 142 can be varied by rotating a handle 83. Since the pulling force is lowered as the distance is enlarged and the pulling force is raised as the distance is reduced, an appropriate pulling force can be set.

Note that the present disclosure is not limited only to the aforementioned embodiments, and various modifications can be made by one skilled in the art within the scope of the technical thought of the present disclosure. For instance, while the coating with the coating liquid R is conducted gradually from the distal side toward the proximal side of the balloon 30 in the aforementioned embodiments, the coating may be performed gradually from the proximal side toward the distal side.

In addition, while the pulling force is constant in the coating step in the aforementioned embodiments, the pulling force may be varied, for example, according to that part of the balloon 30 which is being coated with the coating liquid R.

In addition, while the pulling force is applied to the balloon 30 by moving a distal portion of the balloon 30 distally while limiting movement of a proximal portion of the balloon 30 in the direction of the axis X in the aforementioned embodiments, the pulling force may be applied to the balloon 30 by, for example, moving the proximal portion of the balloon 30 proximally while limiting movement of the distal portion of the balloon 30 in the direction of the axis X. In this case, for example, the rotating mechanism 60 grasping the hub 40 may be configured to be movable proximally, whereby it is possible to apply a pulling force to the balloon 30 by moving the proximal portion of the balloon 30 proximally.

In addition, while the pulling force is applied to the balloon 30 through the elastic member 86 by moving the pulling member 85 in the first embodiment, the pulling force can also be applied directly to the balloon 30 according to the pulling distance based on the movement of the pulling member 85, without providing the elastic member 86. Even without providing the elastic member 86, bend of the balloon 30 can be straightened and the balloon 30 can be restrained from getting eccentric, if a pulling force or a pulling distance can be applied to the balloon 30.

Figure 5:
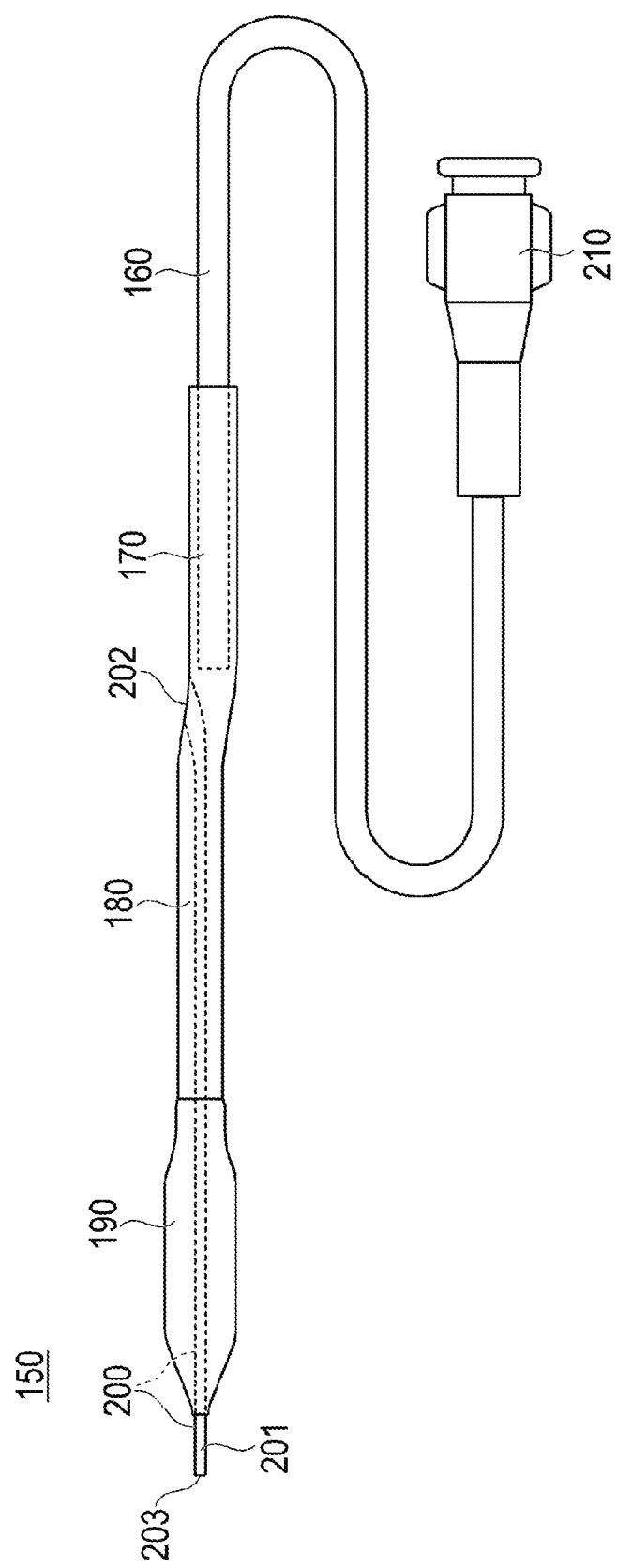
FIG. 5 is a plan view showing another example of the balloon catheter.

In addition, while the balloon 30 of the balloon catheter 10 of an over-the-wire type is subjected to the coating in the balloon coating methods according to the aforementioned embodiments, a balloon 190 of a balloon catheter 150 of a rapid exchange type, as illustrated in FIG. 5, may be subjected to the coating. The balloon catheter 150 can include a hub 210, a proximal shaft 160, an intermediate portion 170, a distal shaft 180, the balloon 190, and an inner tube shaft 200, from a proximal side.

To the hub 210, the proximal shaft 160 formed of a material having a comparatively high rigidity such as metals and some of resins is joined in such a communication as to permit flow of fluid therethrough.

On the distal side of the proximal shaft 160, the intermediate portion 170 is provided in such a communication as to permit flow of fluid therethrough. On the distal side of the intermediate portion 170, the distal shaft 180 formed of a material such as resin and having a comparatively low rigidity is provided in such a communication as to permit flow of fluid therethrough. On the distal side of the distal shaft 180, a proximal portion of the balloon 190 is provided in such a communication as to permit flow of fluid therethrough.

The inner tube shaft 200 coaxially penetrates the inside of the distal shaft 180 and the balloon 190. A distal portion of the inner tube shaft 200 constitutes a tip 201, which extends distally beyond a distal portion of the balloon 190. The tip 201 is jointed to the distal portion of the balloon 190 in a liquid-tight state. A proximal end of the inner tube shaft 200 is extended to a guide wire opening portion 202 provided at a part of a portion ranging from the intermediate portion 170 to the distal shaft 180, and is joined to the guide wire opening portion 202 in a liquid-right manner. A guide wire can be inserted into the inner tube shaft 200, with a distal opening portion 203 of the tip 201 as an entrance and with the guide wire opening portion 202 as an exit.

Even the balloon catheter 150 of the rapid exchange type aforementioned can be mounted to the balloon coating apparatus 50 by a method wherein the balloon 190 is inflated and sealed, the hub 210 is attached to the rotating mechanism 60, at least part of the proximal shaft 160, the intermediate portion 170 and the distal shaft 180 is supported by a support base 70, and a core member 61 is inserted into the inner tube shaft 200 via the guide wire opening portion 202. Then, a coating layer can be formed on an outer surface of the balloon 190 by a method which is the same or equivalent to the methods described in the aforementioned embodiments.

The detailed description above describes a balloon coating method and a balloon coating apparatus for forming a coating layer on a surface of a balloon. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A balloon coating method for forming a coating layer on an outer surface of a balloon of a balloon catheter, the balloon coating method comprising:
    a pulling step of pulling an inner tube of the balloon in an axial direction of the balloon to thereby straighten a bend of the balloon, the inner tube of the balloon having a core member extending in the inner tube, and wherein the core member is not pulled during the pulling of the balloon; and
    a coating step of rotating the balloon about an axis of the balloon, with the balloon maintained in a bend-straightened state, and coating the outer surface of the balloon with a coating liquid containing a drug.

2. The balloon coating method according to claim 1, wherein in the pulling step, a pulling force is arbitrarily controlled.

3. The balloon coating method according to claim 1, wherein in the coating step, a member for applying a pulling force to the balloon is rotated at a same rotational speed as that of the balloon, by a second rotating mechanism differing from a first rotating mechanism for rotating the balloon.

4. The balloon coating method according to claim 1, wherein in the pulling step, the balloon is straightened such that a deflection amount of the balloon is not more than 0.5 mm.

5. The balloon coating method according to claim 1, wherein in the pulling step, a pulling force is applied to the balloon through an elastic member.

6. The balloon coating method according to claim 1, further comprising:
    pulling a distal end of the balloon together with the inner tube of the balloon with the core member extending in the inner tube.

7. The balloon coating method according to claim 1, wherein the balloon includes a catheter main body section, the catheter main body section comprising an outer tube and the inner tube, and an inflation lumen between the outer tube and the inner tube, and wherein the balloon is provided at a distal portion of the catheter main body section, and wherein a length of the balloon is not less than 100 mm.

8. A balloon coating method for forming a coating layer on an outer surface of a balloon of a balloon catheter, the balloon coating method comprising:
    pulling an inner tube of the balloon in an axial direction of the balloon to thereby straighten a bend of the balloon, the inner tube of the balloon having a core member extending in the inner tube, and wherein the core member is not pulled during the pulling of the balloon;
    rotating the balloon about an axis of the balloon;
    maintaining the balloon in a bend-straightened state; and
    coating the outer surface of the balloon with a coating liquid containing a drug.

9. The balloon coating method according to claim 8, comprising:
    controlling a pulling force on the balloon according to the balloon and the pulling force to straighten the bend of the balloon.

10. The balloon coating method according to claim 8, comprising:
    rotating a member for applying a pulling force to the balloon at a same rotational speed as that of the balloon, by a second rotating mechanism differing from a first rotating mechanism for rotating the balloon.

11. The balloon coating method according to claim 8, wherein the balloon is straightened such that a deflection amount of the balloon is not more than 0.5 mm.

12. The balloon coating method according to claim 8, comprising:
    applying a pulling force to the balloon through an elastic member.

13. The balloon coating method according to claim 8, further comprising:
    pulling a distal end of the balloon together with the inner tube of the balloon with the core member extending in the inner tube.

14. A balloon coating apparatus for forming a coating layer on an outer surface of a balloon of a balloon catheter, the balloon coating apparatus comprising:
    a first rotating mechanism for rotating the balloon about an axis of the balloon;
    a pulling mechanism for pulling an inner tube of the balloon in an axial direction of the balloon, with the balloon maintained in a rotatable state, the inner tube of the balloon having a core member extending in the inner tube, and wherein the core member is not pulled during the pulling of the balloon; and
    a coating mechanism for coating the outer surface of the balloon with a coating liquid containing a drug.

15. The balloon coating apparatus according to claim 14, wherein the pulling mechanism is capable of arbitrarily controlling the pulling force.

16. The balloon coating apparatus according to claim 15, further comprising:
    a second rotating mechanism that rotates a member for applying a pulling force to the balloon at a same rotational speed as that of the balloon.

17. The balloon coating apparatus according to claim 14, further comprising:
    a second rotating mechanism that rotates a member for applying a pulling force to the balloon at a same rotational speed as that of the balloon.

18. The balloon coating apparatus according to claim 14, wherein the pulling mechanism includes an elastic member for applying a pulling force to the balloon.

19. The balloon coating apparatus according to claim 14, wherein the balloon includes a catheter main body section comprising an outer tube and the inner tube, and an inflation lumen between the outer tube and the inner tube, and wherein the balloon is provided at a distal portion of the catheter main body section, and wherein a length of the balloon is not less than 100 mm.

20. The balloon coating apparatus according to claim 14, wherein the first pulling mechanism is configured to:
    pull a distal end of the balloon together with the inner tube of the balloon with the core member extending in the inner tube.

* * * * *